United States Patent
Oppong et al.

(10) Patent No.: US 10,212,937 B2
(45) Date of Patent: *Feb. 26, 2019

(54) MICROBICIDAL AQUEOUS SOLUTIONS INCLUDING A MONOCHLORAMINE AND A PERACID, AND METHODS OF USING THE SAME

(71) Applicant: Buckman Laboratories International, Inc., Memphis, TN (US)

(72) Inventors: David Oppong, Cordova, TN (US); Luis Zugno, Germantown, TN (US); Thomas E. McNeel, Memphis, TN (US); Shawn Paul Frenzel, Fayetteville, AR (US)

(73) Assignee: Buckman Laboratories International, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,951

(22) Filed: Oct. 28, 2016

(65) Prior Publication Data

US 2017/0118990 A1 May 4, 2017

Related U.S. Application Data

(63) Continuation-in-part of application No. 15/294,212, filed on Oct. 14, 2016, now Pat. No. 9,955,698.

(60) Provisional application No. 62/247,351, filed on Oct. 28, 2015.

(51) Int. Cl.
| | |
|---|---|
| *A01N 59/00* | (2006.01) |
| *A23B 7/154* | (2006.01) |
| *A23B 4/20* | (2006.01) |
| *A23B 9/26* | (2006.01) |
| *A23B 9/30* | (2006.01) |
| *A23B 7/157* | (2006.01) |
| *A23B 4/24* | (2006.01) |
| *A23L 3/3508* | (2006.01) |
| *A23L 3/358* | (2006.01) |
| *A01N 37/16* | (2006.01) |

(52) U.S. Cl.
CPC ............ *A01N 59/00* (2013.01); *A01N 37/16* (2013.01); *A23B 4/20* (2013.01); *A23B 4/24* (2013.01); *A23B 7/154* (2013.01); *A23B 7/157* (2013.01); *A23B 9/26* (2013.01); *A23B 9/30* (2013.01); *A23L 3/3508* (2013.01); *A23L 3/358* (2013.01)

(58) Field of Classification Search
CPC .......... A01N 59/00; A01N 37/16; A23B 7/10; A23B 7/157; A23B 9/30; A23B 9/26; A23B 4/24; A23B 4/12; A23L 3/358; A23L 3/3508; A23V 2002/00

See application file for complete search history.

(56) References Cited

U.S. PATENT DOCUMENTS

| | | | |
|---|---|---|---|
| 3,459,632 A | * | 8/1969 | Jarowenko ............ C08B 31/00 127/32 |
| 8,709,206 B2 | | 4/2014 | Xia et al. |
| 2002/0086903 A1 | | 7/2002 | Giambrone et al. |
| 2010/0078393 A1 | | 4/2010 | Yin |
| 2014/0196751 A1 | | 7/2014 | Dull et al. |

FOREIGN PATENT DOCUMENTS

| | | | | |
|---|---|---|---|---|
| CN | 102067870 | * | 5/2011 | ............ A01N 25/00 |
| CN | 102120639 A | | 7/2011 | |
| CN | 104054750 A | | 9/2014 | |
| GB | 2207354 A | | 2/1989 | |
| WO | 2009099419 A2 | | 8/2009 | |
| WO | 2010/080305 A2 | | 7/2010 | |
| WO | 2011/037819 A1 | | 3/2011 | |
| WO | 2011041252 A1 | | 4/2011 | |
| WO | 2013/045638 A1 | | 4/2013 | |
| WO | 2013113592 A1 | | 8/2013 | |
| WO | 2013/184605 A1 | | 12/2013 | |
| WO | 2016118382 A1 | | 7/2016 | |

OTHER PUBLICATIONS

English Abstract of CN 102067870 in Espacenet, Accessed Mar. 30, 2017, pp. 1-2.*
International Search Report and Written Opinion issued in corresponding International Patent Application No. PCT/US2016/057139 dated Dec. 16, 2016 (11 pages).
Russell et al, "Monochloramine Versus Sodium Hypochlorite as Antimicrobial Agents for Reducing Populations of Bacteria on Broiler Chicken Carcasses," Journal of Food Protection, vol. 68, No. 4, Apr. 2005, pp. 758-763.
International Search Report and Written Opinion issued in corresponding International Patent Application No. PCT/US2016/059261 dated Feb. 2, 2017 (13 pages).
Ercken et al. "Effects of peracetic acid and monochloramine on the inactivation of Naegleria lovaniensis," Water Science and Technology, vol. 47, No. 3, (2003), pp. 167-171.
Database CAplus Chemical Abstracts Service (CAS), Columbus, Ohio, US, Database Accession No. 2014:1606322, English Abstract of CN 104054750.

* cited by examiner

*Primary Examiner* — Rachael E Bredefeld
(74) *Attorney, Agent, or Firm* — Kilyk & Bowersox, P.L.L.C.

(57) ABSTRACT

Microbicidal aqueous solutions including (a) monochloramine and (b) at least one peracid, are described. Components (a) and (b) can be present in an effective amount to control the growth of at least one microorganism and the aqueous solution is at a pH of from about 5 to about 12. Methods for controlling the growth of microorganisms are also disclosed.

32 Claims, No Drawings

MICROBICIDAL AQUEOUS SOLUTIONS INCLUDING A MONOCHLORAMINE AND A PERACID, AND METHODS OF USING THE SAME

This application is a continuation-in-part of U.S. patent application Ser. No. 15/294,212, filed Oct. 14, 2016, which claims the benefit under 35 U.S.C. § 119(e) of prior U.S. Provisional Patent Application No. 62/247,351, filed Oct. 28, 2015, which are incorporated in their entireties by reference herein.

BACKGROUND OF THE INVENTION

The present invention relates to aqueous solutions or formulations and methods for controlling the growth of microorganisms on a variety of mediums, substrates and in liquid systems. More particularly, the invention relates to using monochloramine and peracid, such as peracetic acid, in aqueous treatment solutions.

Many industrial materials and media when wet or subjected to treatment in water are susceptible to bacterial, fungal, and/or algal deterioration or degradation. A large variety of commercial, industrial, agricultural, and wood materials or products are subject to microbiological attack or degradation which reduces or destroys their economic value. These industrial materials and media include, but are not limited to, for example, wood pulp, wood chips, lumber, adhesives, coatings, animal hides, paper mill liquors, pharmaceutical formulations, cosmetic formulations, toiletry formulations, geological drilling lubricants, petrochemicals, agrochemical compositions, paints, leathers, plastics, seeds, plants, wood, metalworking fluids, cooling water, recreational water, influent plant water, waste water, pasteurizers, retort cookers, tanning liquors or solutions, starch, proteinaceous materials, acrylic latex paint emulsions, and textiles. The various temperatures at which such materials or products are manufactured, stored, or used as well as their intrinsic characteristics make them susceptible to growth, attack, and degradation by common microorganisms such as algae, fungi, yeasts, and bacteria. These microorganisms may be introduced during a manufacturing or other industrial process, by exposure to air, tanks, pipes, equipment, and humans. They can also be introduced while using a material or product, for example, by multiple openings and reclosures of packages or from stirring or removing material with contaminated objects.

To control deterioration or degradation caused by microorganisms, various industrial microbicides are used. Workers in the trade have continued to seek improved biocides that have low toxicity, are cost effective, and are also capable of exhibiting a prolonged biocidal effect against a wide variety of microorganisms with regular use.

Aqueous systems are also highly subject to microbiological growth, attack, and degradation. These aqueous systems may be fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiological growth and thus attack and degradation.

Microbiological degradation of aqueous systems may manifest itself as a variety of problems, such as loss of viscosity, gas formation, objectionable odors, decreased pH, emulsion breaking, color change, and gelling. Additionally, microbiological deterioration of aqueous systems can cause fouling of the related water-handling system, which may include cooling towers, pumps, heat exchangers, and pipelines, heating systems, scrubbing systems, and other similar systems.

Another objectionable phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms. Slime reduces yields in production and causes plugging, bulking, and other problems in industrial water systems.

Despite the existence of such microbicides, industry is constantly seeking more cost-effective technology which offers equal or better protection at lower cost and lower concentration. The concentration of conventional microbicides and the corresponding treatment costs for such use, can be relatively high. Important factors in the search for cost-effective microbicides include the duration of microbicidal effect, the ease of use and the effectiveness of the microbicide per unit weight.

SUMMARY OF THE INVENTION

It is a feature of this invention to provide a microbicidal aqueous solution capable of controlling the growth of at least one microorganism, for example, fungi, bacteria, algae, or mixtures thereof, for example, over short or over prolonged periods of time. It is an additional feature of this invention to provide such aqueous solutions which are economical to use. Methods of controlling the growth of at least one microorganism are also features of this invention.

Aqueous solutions and processes useful for controlling the growth of one or more microorganisms are described. Aqueous solutions and methods for preventing damage during storage caused by microorganisms, such as bacteria, fungi, algae, or mixtures thereof, are described.

The present invention, in part, relates to an aqueous solution or formulation and more particularly, a microbicidal aqueous solution or formulation.

The present invention provides an aqueous solution comprising (a) monochloramine and (b) at least one peracid, wherein components (a) and (b) are present in a microbicidally effective combined amount to control the growth of at least one microorganism. The pH of the aqueous solution preferably is from about 5 to about 12.

The present invention also provides an aqueous solution or formulation comprising a) monochloramine and b) at least one peracid such as peracetic acid, where components a) and b) are present in a combined amount preferably synergistically effective to control the growth of at least one microorganism.

The present invention provides a method of controlling the growth of at least one microorganism in or on a product, material, or medium susceptible to attack by a microorganism. This method includes the step of treating the product, material or medium with an aqueous solution comprising (a) monochloramine and (b) at least one peracid, wherein components (a) and (b) are present in a microbicidally effective combined amount to control the growth of at least one microorganism. The pH of the aqueous solution or the product, material or medium, or both, preferably is from about 5 to about 12.

The present invention further provides a method for controlling the growth of at least one microorganism in or on a product, material, or medium susceptible to attack by the microorganism. The method includes the step of adding to the product, material, or medium an aqueous solution comprising a) monochloramine and b) at least one peracid, preferably in amounts synergistically effective to control the growth of the microorganism. The synergistically effective amount of a) and b) varies in accordance with the product, material, or medium to be treated and can, for a particular application, be routinely determined by one skilled in the art in view of the disclosure provided herein.

The present invention, in addition, provides a method for preventing or slowing down spoilage of a product, material, or medium caused by microorganism selected from bacteria, fungi, algae, or mixtures thereof, which includes the step of applying an aqueous solution to the product, material, or medium, and the aqueous solution comprising (a) monochloramine and (b) at least one peracid, wherein components (a) and (b) are present in a microbicidally effective combined amount to control the growth of at least one microorganism. The pH of the aqueous solution or the product, material, or medium, or both, preferably is from about 5 to about 12.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

It is understood that both the foregoing general description and the following detailed description are exemplary and explanatory only, and are not restrictive of the present invention as claimed.

DETAILED DESCRIPTION

The present invention provides an aqueous solution to control the growth of at least one microorganism comprising a mixture (or a formulation) of a) at least one monochloramine and b) at least one per acid, such as peracetic acid. The monochloramine and peracid can be present in a microbicidally effective combined amount to control the growth of at least one microorganism. The pH of the aqueous solution can be from about 5 to about 12, such as from about 7 to about 10, or from 7.1 to 12, or from 7.5 to 10, or from 8 to 10. The aqueous solution can further include least one pH control agent, such as at least one base or at least one acid. The aqueous solution can include at least one base, such as sodium hydroxide and/or other base. The addition or presence of at least one base along with the monochloramine and peracid in the aqueous solution can provide optimal control of pathogenic bacteria. The monochloramine and peracid can be preferably present in a combined amount synergistically effective to control the growth of at least one microorganism. The combined use of a) monochloramine and b) at least one peracid can provide superior microbicidal activity at low concentrations or other concentrations against a wide range of microorganisms. The term "aqueous solution" as used herein can, as an example, refer to a solution that is predominantly water (e.g., over 50% by volume water such as over 75% by volume, over 95% by volume, or over 99% by volume water) and retains the solution characteristics of water. Where the aqueous solution contains solvents in addition to water, water is typically the predominant solvent.

The aqueous solutions comprising monochloramine and peracid of the present invention can be used in a method for controlling the growth of at least one microorganism in or on a product, material, or medium susceptible to attack by the microorganism. This method includes the step of adding to, applying to, or otherwise contacting the product, material, or medium with a) monochloramine and b) at least one peracid, and, if used, at least one base. The pH of the an aqueous solution or the product, material or medium, or both, can be from about 5 to about 12, such as from about 7 to about 10, or from 7.1 to 12, or from 7.5 to 10, or from 8 to 10. The components a) and b) can be present in microbicidally or synergistically effective combined amounts to control the growth of the microorganism.

The microbicidally or synergistically effective amount varies in accordance with the material or medium to be treated and can, for a particular application, be routinely determined by one skilled in the art in view of this disclosure.

In lieu of adding the aqueous solution of the present invention to a material or medium to be treated, the monochloramine and peracid, such as peracetic acid, and, if used, at least one base, can be separately added to the product, material, or medium to be treated. These components are individually added so that the final amount of the mixture of monochloramine and peracid acid at the time of use can preferably be that amount microbicidally or synergistically effective to control the growth of at least one microorganism.

As stated earlier, the combined use of a) monochloramine and b) at least one peracid in an aqueous solution is useful in preserving various type of products, media, or materials susceptible to attack by at least one microorganism. The combined use of a) monochloramine and b) at least one peracid is also useful in agrochemical formulations for the purpose of protecting seeds or crops against microbial spoilage. These methods of preserving and protecting are accomplished by adding or otherwise contacting an aqueous solution comprising a) monochloramine and b) at least one peracid to the products, media, or materials in an amount that can preferably be microbicidally or synergistically effective to preserve or control the products, media, or materials from attack by at least one microorganism or to effectively protect the seeds or crops against microbial spoilage.

In the present invention, aqueous solutions comprising a) monochloramine and b) at least one peracid (and optionally at least one base or pH control agent) are useful in preserving or controlling the growth of at least one microorganism in various types of industrial and/or food products, media, or materials susceptible to attack by microorganisms. Such media or materials include, but are not limited to, for example, dyes, pastes, lumber, leathers, textiles, pulp, wood chips, tanning liquor, paper mill liquor, fiberglass, dairy processing, poultry processing, meat processing (e.g., beef, pork, lamb, or chicken), meat packing plant, animal slaughter houses, polymer emulsions, paints, paper and other coating and sizing agents, metalworking fluids, geological drilling lubricants, petrochemicals, cooling water systems, recreational water, influent plant water, waste water, pasteurizers, retort cookers, pharmaceutical formulations, cosmetic formulations, and toiletry formulations.

The combined use of a) monochloramine and b) at least one peracid (and optionally the at least one base or pH control agent) in aqueous solutions can also be used to treat or preserve materials and media that include, but are not limited to, for example, wood pulp, wood chips, lumber, adhesives, coatings, animal hides, paper mill liquors, pharmaceutical formulations, cosmetic formulations, toiletry formulations, geological drilling lubricants, petrochemicals, agrochemical compositions, paints, leathers, plastics, seeds, plants, wood, metalworking fluids, cooling water, recreational water, influent plant water, waste water, pasteurizers, retort cookers, tanning liquors or solutions, starch, proteinaceous materials, acrylic latex paint emulsions, and textiles.

The combined use of a) monochloramine and b) at least one peracid (and optionally at least one base or pH control agent) in aqueous solutions can be used to treat or preserve aqueous systems, such as ones subject to microbiological growth, attack, and degradation. These aqueous systems may be or include, but are not limited to, fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. Additionally, with the present invention, microbiological deterioration of aqueous systems can be prevented or controlled including, but not limited to, related water-handling system, which may include cooling towers, pumps, heat exchangers, and pipelines, heating systems, scrubbing systems, and other similar systems, and the like.

The combined use of a) monochloramine and b) at least one peracid (and optionally the at least one base or pH control agent) in aqueous solutions can also be used to protect or treat or preserve foods and/or surfaces in contact with food, such as fresh foods (e.g., vegetables and fruits) or meats, or dairy products or processing, for instance, to extend shelf life. The present invention can be used to protect or treat facilities that process food (meats, fruits, vegetables) including but not limited to the surfaces and machinery and devices that come into contact with the food or animal.

The combined use of a) monochloramine and b) at least one peracid (and optionally at least one base or pH control agent) in aqueous solutions can also be useful in agrochemical formulations for the purpose of protecting seeds or crops against microbial spoilage.

According to the methods of the present invention, controlling or inhibiting the growth of at least one microorganism includes the reduction and/or the prevention of such growth.

It is to be further understood that by "controlling" (i.e., preventing) the growth of at least one of microorganism, the growth of the microorganism is inhibited. In other words, there is no growth or essentially no growth of the microorganism. "Controlling" the growth of at least one microorganism maintains the microorganism population at a desired level, reduces the population to a desired level (even to undetectable limits, e.g., zero population), and/or inhibits the growth of the microorganism. Thus, in the present invention, the products, material, or media susceptible to attack by the at least one microorganism can be preserved from this attack and the resulting spoilage and other detrimental effects caused by the microorganism. Further, it is also to be understood that "controlling" the growth of at least one microorganism also includes biostatically reducing and/or maintaining a low level of at least one microorganism such that the attack by the microorganism and any resulting spoilage or other detrimental effects are mitigated, i.e., the microorganism growth rate or microorganism attack rate is slowed down and/or eliminated.

When two chemical microbicides are mixed and added to the product, or added separately, three results are possible:
1) The chemicals in the product would produce an additive (neutral) effect.
2) The chemicals in the product would produce an antagonistic effect, or
3) The chemicals in the product would produce a synergistic effect.

An additive effect has no economic advantage over the individual components. The antagonistic effect would produce a negative impact. Only a synergistic effect, which is less likely than either an additive or antagonistic effect, would produce a positive effect and therefore possess economic advantages.

It is known in the microbicidal literature that there is no theoretical method to anticipate additive, antagonistic, or synergistic effects when two biocides are mixed to yield a new formulation. Nor is there a method to predict the relative proportions of the different biocides required to produce one of the three effects described above.

Thus, the combination of a) monochloramine and b) at least one peracid (and optionally at least one base or pH control agent) in aqueous solutions preferably achieve superior, i.e. greater than additive, microbicidal activity, even at low concentrations, against a wide variety of microorganisms. Examples of these microorganisms include fungi, bacteria, algae, and mixtures thereof, such as, but not limited to, for example, *Trichoderma viride, Aspergillus niger, Pseudomonas aeruginosa, Enterobacter aerogenes, Klebsiella pneumoniae,* and *Chlorella* sp. The combination of a) monochloramine and b) at least one peracid of the present invention can have a low toxicity.

The monochloramine ($NH_2Cl$) (also referred to here as MCA) can be obtained or made on site. In dilute aqueous solution, chloramine is prepared by the reaction of ammonia with sodium hypochlorite:

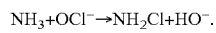

$$NH_3 + OCl^- \rightarrow NH_2Cl + HO^-.$$

This is also the first step of the Raschig hydrazine synthesis. The reaction is carried out in a slightly alkaline medium (pH 8.5 to 11). The acting chlorinating agent in this reaction is hypochloric acid (HOCl), which has to be generated by protonation of hypochlorite, and then reacts in a nucleophilic substitution of the hydroxo against the amino group. The reaction occurs quickest at around pH 8. At higher pH values the concentration of hypochloric acid is lower, at lower pH values ammonia is protonated to form ammonium ions $NH_4^+$, which do not react further. The chloramine solution can be concentrated by vacuum distillation and by passing the vapor through potassium carbonate which absorbs the water. Chloramine can be extracted with ether. Gaseous chloramine can be obtained from the reaction of gaseous ammonia with chlorine gas (diluted with nitrogen gas):

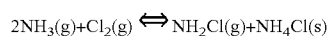

$$2NH_3(g) + Cl_2(g) \rightleftharpoons NH_2Cl(g) + NH_4Cl(s)$$

Pure chloramine can be prepared by passing fluoroamine through calcium chloride:

$$2NH_2F + CaCl_2 \rightarrow 2NH_2Cl + CaF_2.$$

Methods for in situ chloramine generation are known which can be adapted for use in the method of the present invention. For example, rather than adding pure chloramine to the product, material, or system, sodium hypochlorite solution or chlorine can be added together with ammonia or ammonium salts to generate chloramine in situ prior to or at the time of combining with the peracid. A single type of chloramine or combinations of different chloramines can be used.

"Peracid" and "organic peracid" refer to compounds of the structure R—CO—OOH, in which R is an organic radical. Examples include a peracid of an organic aliphatic monocarboxylic acid having 2 to 10 carbon atoms (i.e., R is an organic radical having from 1 to 9 carbon atoms), such as acetic acid (ethanoic acid), propionic acid (propanoic acid), butyric acid (butanoic acid), iso-butyric acid (2-methyl-propanoic acid), valeric acid (pentanoic acid), 2-methyl-butanoic acid, iso-valeric acid (3-methyl-butanoic acid), and 2,2-dimethyl-propanoic acid. The peracid can be or include peracetic acid ($CH_3CO$—OOH). Mixtures of peracids may be used. For example, peracetic acid may be mixed with other organic acids and their corresponding peracids, such as with one or more peracids derived from aliphatic monocarboxylic acids having 3 to 10 carbon atoms (i.e. aliphatic monocarboxylic peracids having 3 to 10 carbon atoms), for example, perhexanoic acid, perheptanoic acid, per(2-ethyl) hexanoic acid, peroctanoic acid, pernonaoic acid, and/or perdecanoic acid. One combination can be peracetic acid with peroctanoic acid ($C_7H_{15}CO$—OOH).

A peracid can function better in an acidic environment, whereas MCA can function better in alkaline environment. For purposes of the present invention, it has been discovered that even better results can be achieved when the pH of the aqueous solution and/or the product, material, or medium coming in contact with the aqueous solution of the present invention is from about 7 to about 12, such as from about 7 to about 10, or from 7.1 to 12, or from 7.5 to 10, or from 8 to 10. This desirable pH range can be achieved in any manner known. Preferably, at least one base or other pH adjusting agent can be used or added to achieve this pH range.

At least one base can be present or included in the aqueous solution, for instance, to adjust, e.g., fine-tune, the pH for optimal effect or synergy between the peracid and MCA from a biocidal efficiency standpoint, or cost perspective, or both. Further, pH control can be used to control volatilization of some peracids, such as peracetic acid. Any base can be used herein as a pH-adjusting adjunct for adjusting the pH (e.g., increasing pH). The base can be an alkali metal hydroxide, alkaline earth metal hydroxide, or any combination thereof. The base can be sodium hydroxide, potassium hydroxide, calcium hydroxide, barium hydroxide, magnesium hydroxide, sodium carbonate, or any combination thereof. Preferred bases for pH adjustment can include water-soluble alkalis such as sodium hydroxide, potassium hydroxide, or mixtures thereof. The base can be used as an aqueous solution. The base can be added to the aqueous solution before treatment of a product, material or medium, and/or can be added to the product, material or medium before or after treatment with the aqueous solution, or both. As indicated, the base can be used as a pH control agent. If desirable to reduce the pH, such as, e.g., to provide or maintain a pH of no greater than 12 or other pH value with a range of about 5 to about 12, a pH control agent can used which is at least one acid. The at least one acid, if used, can be acetic acid, citric acid, hydrochloric acid, sulfuric acid, or other acids, or alum, or any combination thereof.

The amount of base added can be the amount needed to adjust the aqueous solution to the desired pH value or range. The concentration of the base can be any commercially available concentration (e.g., 0.1 N or 0.01N, or concentrated base) and/or can be diluted to any desired or appropriate concentration. The base can be present in a concentration so that the aqueous solution has a pH of from about 5 to about 12, or from about 6 to about 11, or from about 7 to about 10, or from about 7.1 to about 9.9, or from about 7.5 to about 9.5, or from about 8 to about 9, or other values.

The aqueous solution to which the at least one base is added can be a reservoir or flowing stream of aqueous fluid which already contains monochloramine but not yet peracid. For instance, after the at least one base is added to the aqueous fluid comprising monochloramine, the resulting base-treated aqueous fluid can be further modified by addition of the peracid before the aqueous fluid comprising all three components is introduced into an aqueous system (or product, material, or medium) to be treated. As another option, aqueous fluid comprising the monochloramine and the least one base can be added to the aqueous system (or product, material, or medium) to be treated, and the peracid can be separately added to the aqueous system upstream or downstream thereof. As another option, the at least one base, monochloramine, and peracid can be separately added to an aqueous system (or product, material, or medium) to be treated, wherein the aqueous solution is essentially prepared concurrent with treatment by it. The aqueous system or medium that can be treated in any of these manners with the aqueous solution can be aqueous fluid (e.g., water alone, or water-predominant solutions, or other water-based solutions) held in a pool, vessel, or flowing aqueous fluid in a conduit or open flowing stream, or other aqueous systems. The liquid system or medium may be an animal water trough or gutter through which drinking water flows or stands. As stated, the present invention also embodies the separate addition of the monochloramine and at least one peracid, such as peracetic acid, and, if used, the at least one base or pH control agent, to products, materials, or media. According to this option, the components are individually added to the products, materials, or media so that the final amount of each component present at the time of use that can preferably be that amount microbicidally or synergistically effective, to control the growth of at least one microorganism.

The monochloramine and at least one peracid, and, if used, the at least one base or pH control agent, can be added separately to the product, material, or medium, or system or environment that contains the product, material or medium. When adding separately, each of the monochloramine and peracid, and, if used, the at least one base or pH control agent, can be added simultaneously, almost simultaneously (within 0.1 sec to 5 minutes of each other, for instance within 5 seconds, within 10 seconds, within 30 seconds, within 1 minute, within 2 minutes, within 5 minutes, or within 10 minutes of each other), or in sequence and in any order (e.g., monochloramine first or peracid first). Further, in this option or in any embodiment of the present invention, the monochloramine can be formed in-situ in the presence of (or just before the MCA contacts) the product, material, or medium being treated or protected. The in-situ formation of the monochloramine can be done before or after peracid is present. After adding (or forming) each of the monochloramine and peracid, and, if used, the at least one base or pH control agent, in a liquid solution, medium or environment, mixture or agitation can be optionally used to mix the two (or three) components together for any amount of time (e.g., 1 second to 10 minutes or more). Each component can be applied by spraying, misting, coating, dipping, or any other technique/application that permits the contacting of the product, material, medium or system with each of a) monochloramine and b) at least one peracid.

The microbicides in the aqueous solution of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. The solvent can be selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

A microbicide component also can be formulated in the form of a dispersion. The solvent component of the dispersion can be an organic solvent or water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and/or anti-corrosion additives.

When a microbicide component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

As described above, components (a) monochloramine (MCA) and (b) at least one peracid (and optionally the at least one base or pH control agent) are preferably used in aqueous solution in microbicidally or synergistically effective amounts. The weight ratios of (a) to (b) vary depending on the type of microorganisms and product, material, or media to which the aqueous solution is applied. In view of the present invention, one skilled in the art can readily determine, without undue experimentation, the appropriate weight ratios for a specific application. The weight ratio of component (a) to component (b) used in aqueous solution preferably ranges from 1:99 to 99:1, more preferably from 1:30 to 30:1, and most preferably 1:2 to 2:1. For instance, in an aqueous solution or formulation, the MCA can be present at a concentration of from 0.1 ppm to 50,000 ppm, or from 0.1 ppm to 10,000 ppm, or from 0.1 ppm to 5,000 ppm, or from 0.1 ppm to 1,000 ppm, or from 0.1 ppm to 500 ppm, or from 0.1 ppm to 100 ppm, or from 0.1 ppm to 75 ppm, or from 0.1 ppm to 50 ppm, or from 1 ppm to 5,000 ppm, or from 5 ppm to 500 ppm, and the peracid can be present at a concentration of from 0.1 ppm to 10,000 ppm, or from 0.1 ppm to 5,000 ppm, or from 0.5 ppm to 7,500 ppm, or from 1 ppm to 6,000 ppm, or from 2 ppm to 5,000 ppm, or from 3 ppm to 4,000 ppm, or from 4 ppm to 3,000 ppm, or from 5 ppm to 2,000 ppm, or from 1 ppm to 500 ppm, or from 5 ppm to 100 ppm.

In general, for the aqueous solution having a pH of from about 5 to about 12 and, if used, base or pH control agent, a microbicidally effective response (e.g., fungicidal, bactericidal, or algicidal response) can be obtained when the combination of component (a) and component (b) is employed in concentrations ranging about 0.1 ppm to 5% (i.e., 50,000 ppm) of the MCA, preferably from 0.1 ppm to 500 ppm, more preferably from 0.1 ppm to 100 ppm, even more preferably from 0.1 ppm to 75 ppm, and most preferably from 0.1 ppm to 50 ppm; and from 0.1 ppm to 10,000 ppm of the peracid (e.g., peracetic acid), preferably 2 ppm to 5,000 ppm, more preferably 3 ppm to 4,000 ppm, even more preferably 4 ppm to 3,000 ppm, and most preferably 5 ppm to 2,000 ppm. In general, an effective fungicidal, bactericidal, or algicidal response can be obtained when the synergistic combination is employed in concentrations ranging about 0.01 ppm to 1% (i.e., 10,000 ppm) of the MCA, preferably 1 ppm to 5,000 ppm, and most preferably 5 ppm to 500 ppm; and from about 0.1 ppm to 5,000 ppm of the peracid (e.g., peracetic acid), preferably 1 to 500 ppm, and most preferably, 5 ppm to 100 ppm. These ppm concentrations can be for the aqueous solution to be treated and/or can be the ppm concentrations of the aqueous solution prepared and used to treat an aqueous solution.

Depending upon the specific application, the aqueous solution can be prepared in liquid form by dissolving, dispersing, or in-situ forming the monochloramine and at least one peracid, and, if used, at least one base or pH control agent, in water or other aqueous fluid. The preservative containing the aqueous solution of the present invention may be prepared in an emulsion form by emulsifying it in water, or if necessary, by adding a surfactant. Additional chemicals, such as insecticides, may be added to the foregoing preparations and aqueous solutions depending upon the intended use of the preparation.

The mode as well as the rates of application of the aqueous solution of this invention could vary depending upon the intended use. The aqueous solution could be applied by spraying or brushing onto the material or product. The material or product in question could also be treated by dipping in a suitable formulation of the aqueous solution. In a liquid or liquid-like medium, the aqueous solution could be added into the medium by pouring, or by metering with a suitable device so that a solution or a dispersion of the aqueous solution can be produced.

The microbicidal and synergistic activity of the combinations described above has been confirmed using standard laboratory techniques as illustrated below. The following examples are intended to illustrate, not limit, the present invention.

Microbicidal Evaluation
Method

Nutrient broth (2.5 g/liter of deionized water) was prepared and dispensed in 5 ml amounts into test tubes and autoclaved for 20 minutes at 121° C. The biocides were added to the test tubes in the desired concentrations, and then 100 microliters of a 24-hour grown suspension of *Pseudomonas aeruginosa* or *Enterobacter aerogenes* cells were added to the respective test tubes to give a final count of approximately $10^6$ cfu/ml and incubated at 37° C. at the indicated contact times.

The lowest concentration of each mixture or compound which completely prevented growth of the bacteria at the indicated times was taken as the end point for synergism calculations. End points for the various mixtures were then compared with the end points for the pure active ingredients alone in concomitantly prepared flasks or test tubes.

Synergism was demonstrated by the method described by Kull, E. C., et al., APPLIED MICROBIOLOGY 9:538-541 (1961):

$$Q_A/Q_a + Q_B/Q_b$$

wherein $Q_a$=Concentration of compound A in parts per million, acting alone,
which produced an end point.

$Q_b$=Lowest concentration of compound B in parts per million, acting alone,
which produced an end point.

$Q_A$=Lowest concentration of compound A in parts per million, in the mixture,
which produced an end point.

$Q_B$=Lowest concentration of compound B in parts per million, in the mixture,
which produced an end point.

When the sum of $Q_A/Q_a$ and $Q_B/Q_b$ is greater than one, antagonism is indicated. When the sum is equal to one, additivity is indicated. When the sum is less than one, synergism exists.

This procedure for demonstrating synergism of the aqueous solutions of this invention is a widely used and acceptable procedure. More detailed information is provided in the article by Kull et al. Further information concerning this procedure is contained in U.S. Pat. No. 3,231,509, the disclosure of which is herein incorporated in its entirety by reference.

Based on the above criteria, as shown further below, a synergistic activity against bacteria is observed when the monochloramine is combined with the peracetic acid. Examples showing synergistic results can be found in the table below.

Example 1

In Example 1, a synergistic effect was demonstrated by testing the combination of peracetic acid, designated as component A, and monochloramine (MCA), designated as component B in a series of tests in varying ratios and a range of concentrations against the bacterium, *Enterobacter aerogenes*, using the method described above. Contact time was 15 hours. The MCA was obtained by combinations of ammonium sulfate in the form of Oxamine 6150 or Busan 1215 (all from Buckman Laboratories, Memphis, Tenn.) and the oxidant, Bulab 6004 (from Buckman Laboratories). The peracetic acid was from Sigma-Aldrich (32 wt. % in dilute acetic acid) which was diluted in deionized water to desired concentration range prior to adding it to the test systems.

| Quantities producing endpoints (ppm) | | | | | | |
|---|---|---|---|---|---|---|
| $Q_a$ | $Q_A$ | $Q_b$ | $Q_B$ | $Q_A/Q_a$ | $Q_B/Q_b$ | $Q_A/Q_a + Q_B/Q_b$ |
| 25.0 | — | — | — | — | — | — |
|  | 10 |  | 50 | 0.4 | 0.5 | 0.9 |
|  | 5.0 |  | 50 | 0.2 | 0.5 | 0.7 |
|  | 2.5 |  | 50 | 0.1 | 0.5 | 0.6 |
|  | 1.0 |  | 50 | 0.04 | 0.5 | 0.54 |
|  | 10 |  | 25 | 0.4 | 0.25 | 0.65 |
|  | 10.0 |  | 20 | 0.4 | 0.2 | 0.60 |
| — | — | 100 |  |  | 0.5 |  |

Example 2

In Example 2, a synergistic effect was demonstrated by testing the combination of peracetic acid, designated as component A, and monochloramine (MCA), designated as component B in a series of tests in varying ratios and a range of concentrations against the bacterium, *Pseudomonas aeruginosa*, using the method described above. Contact time was 24 hours. The MCA and peracetic acid were obtained in the same manner as Example 1.

| Quantities producing endpoints (ppm) | | | | | | |
|---|---|---|---|---|---|---|
| $Q_a$ | $Q_A$ | $Q_b$ | $Q_B$ | $Q_A/Q_a$ | $Q_B/Q_b$ | $Q_A/Q_a + Q_B/Q_b$ |
| 10 | — | — | — | — | — | — |
|  | 2.5 |  | 25 | 0.25 | 0.5 | 0.75 |
|  | 5 |  | 10 | 0.5 | 0.2 | 0.7 |
| — | — | 50 | — |  |  |  |

The present invention includes the following aspects/embodiments/features in any order and/or in any combination:

1. An aqueous solution comprising (a) monochloramine and (b) at least one peracid, wherein components (a) and (b) are present in a microbicidally effective combined amount to control the growth of at least one microorganism.
2. The aqueous solution of any preceding or following embodiment/feature/aspect, wherein the pH of the aqueous solution is from about 5 to about 12.
3. The aqueous solution of any preceding or following embodiment/feature/aspect, wherein the aqueous solution further comprises at least one base.
4. The aqueous solution of any preceding or following embodiment/feature/aspect, wherein a pH control agent is present in a concentration so that the aqueous solution has a pH of from about 5 to about 12.
5. The aqueous solution of any preceding or following embodiment/feature/aspect, wherein components (a) and (b) are present in a synergistically microbicidally effective combined amount to control the growth of at least one microorganism.
6. The aqueous solution of any preceding or following embodiment/feature/aspect, wherein the peracid is peracetic acid.
7. The aqueous solution of any preceding or following embodiment/feature/aspect, wherein the monochloramine is present in the aqueous solution at a concentration of 0.1 ppm to 50 ppm, and the at least one peracid is present in the aqueous solution at a concentration of from 5 ppm to 2000 ppm.
8. The aqueous solution of any preceding or following embodiment/feature/aspect, wherein the pH is from 7 to 10.
9. The aqueous solution of any preceding or following embodiment/feature/aspect, wherein the base comprises sodium hydroxide.

10. The aqueous solution of any preceding or following embodiment/feature/aspect, wherein the base is present in a concentration so that the aqueous solution has a pH of from about 5 to about 12.
11. The aqueous solution of any preceding or following embodiment/feature/aspect, wherein the base is present in a concentration so that the aqueous solution has a pH of from 7 to 10.
12. The aqueous solution of any preceding or following embodiment/feature/aspect, wherein the pH control agent is at least one base or at least one acid.
13. A method of controlling the growth of at least one microorganism in or on a product, material, or medium susceptible to attack by a microorganism, the method comprising treating the product, material or medium with aqueous solution comprising (a) monochloramine and (b) at least one peracid, wherein components (a) and (b) are present in a microbicidally effective combined amount to control the growth of at least one microorganism.
14. The method of any preceding or following embodiment/feature/aspect, wherein the pH of the aqueous solution or the product, material or medium, or both, is from about 5 to about 12.
15. The method of any preceding or following embodiment/feature/aspect, wherein the peracid is peracetic acid.
16. The method of any preceding or following embodiment/feature/aspect, wherein the monochloramine is present in the aqueous solution at a concentration of from 0.1 ppm to 50 ppm, and the at least one peracid is present in the aqueous solution at a concentration of from 5 ppm to 2000 ppm.
17. The method of any preceding or following embodiment/feature/aspect, wherein the pH is from 7 to 10.
18. The method of any preceding or following embodiment/feature/aspect, wherein the aqueous solution further comprises at least one base.
19. The method of any preceding or following embodiment/feature/aspect, wherein the base comprises sodium hydroxide.
20. The method of any preceding or following embodiment/feature/aspect, wherein the base is present in a concentration so that the aqueous solution has a pH of from about 5 to about 12.
21. The method of any preceding or following embodiment/feature/aspect, wherein the base is present in a concentration so that the aqueous solution has a pH of from 7 to 10.
22. The method of any preceding or following embodiment/feature/aspect, wherein a pH control agent is present in a concentration so that the aqueous solution has a pH of from about 5 to about 12.
23. The method of any preceding or following embodiment/feature/aspect, wherein components (a) and (b) are present in a synergistically microbicidally effective combined amount to control the growth of at least one microorganism.
24. The method of any preceding or following embodiment/feature/aspect, wherein a) and at least one base are combined in an aqueous fluid before adding the aqueous fluid to said product, material, or medium, wherein b) is further added to the aqueous fluid before the adding or separately applied to the said product, material, or medium.
25. The method of any preceding or following embodiment/feature/aspect, wherein said monochloramine is formed in-situ in said medium or in the presence of said product or material.
26. The method of any preceding or following embodiment/feature/aspect, wherein the microorganism is a bacterium.
27. The method of any preceding or following embodiment/feature/aspect, wherein the material or medium is wood pulp or paper, wood chips, lumber, paints, leathers, adhesives, coatings, animal hides, tanning liquor, paper mill liquor, fiberglass, dairy processing, poultry processing, meat packing facilities, meat processing, metalworking fluids, petrochemicals, pharmaceutical formulations, cooling water, recreational water, dyes, clays, mineral slurries, cationic surfactants, formulations with cationic surfactants, influent water, waste water, pasteurizers, retort cookers, cosmetic formulations, toiletry formulations, textiles, geological, drilling lubricants, or agrochemical compositions for crop or seed protection.
28. The method of any preceding or following embodiment/feature/aspect, wherein the material or medium is in the form of a solid, a dispersion, an emulsion, or a solution.
29. A method for preventing or slowing down spoilage of a product, material, or medium caused by microorganism selected from bacteria, fungi, algae, or mixtures thereof, wherein the method comprises applying an aqueous solution to the product, material, or medium, and said aqueous solution comprising (a) monochloramine and (b) at least one peracid, wherein components (a) and (b) are present in a microbicidally effective combined amount to control the growth of at least one microorganism.
30. The method of any preceding or following embodiment/feature/aspect, wherein the pH of the aqueous solution or the product, material, or medium, or both, is from about 5 to about 12.
31. The method of any preceding or following embodiment/feature/aspect, wherein the material is seeds or crops.
32. The method of any preceding or following embodiment/feature/aspect, wherein said product is a meat, vegetable, or fruit.
33. The method of any preceding or following embodiment/feature/aspect, wherein said product is a food product.
34. The method of any preceding or following embodiment/feature/aspect, wherein a) and b) are applied separately to said product, material, or medium.
35. The method of any preceding or following embodiment/feature/aspect, wherein a) and at least one base are combined in an aqueous fluid before adding the aqueous fluid to said product, material, or medium, wherein b) is further added to the aqueous fluid before the adding or separately applied to the said product, material, or medium.
36. The method of any preceding or following embodiment/feature/aspect, wherein said material or medium is a surface, device, and/or machinery utilized in meat, vegetable, or fruit preparation or processing or packing.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. An aqueous solution comprising (a) monochloramine in an amount of 1 ppm to 100 ppm, and (b) at least one peracid in an amount of 1 ppm to 100 ppm, wherein the peracid is peracetic acid and wherein components (a) and (b) are present in a synergistically microbicidally effective combined amount to control the growth of at least one microorganism, wherein said synergistically microbicidally effective combined amount is demonstrated by a formula of $Q_A/Q_a+Q_B/Q_b$, wherein $Q_a$=Concentration of said monochloramine in parts per million, acting alone, which produced an end point to completely prevent growth of a bacteria, $Q_b$=Lowest concentration of said peracid in parts per million, acting alone, which produced an end point to completely prevent growth of said bacteria, $Q_A$=Lowest concentration of said monochloramine in parts per million, in said aqueous solution, which produced an end point to completely prevent growth of said bacteria, $Q_B$=Lowest concentration of said peracid in parts per million, in said aqueous solution, which produced an end point to completely prevent growth of said bacteria, and where the sum of $Q_A/Q_a$ and $Q_B/Q_b$ is less than one, and wherein said bacteria is *Pseudomonas aeruginosa* or *Enterobacter aerogenes*.

2. The aqueous solution of claim 1, wherein the pH of the aqueous solution is from about 5 to about 12.

3. The aqueous solution of claim 1, wherein the aqueous solution further comprises at least one base.

4. The aqueous solution of claim 1, wherein at least one pH control agent is present in a concentration so that the aqueous solution has a pH of from about 5 to about 12.

5. The aqueous solution of claim 2, wherein the pH is from 7 to 10.

6. The aqueous solution of claim 3, wherein the base comprises sodium hydroxide.

7. The aqueous solution of claim 3, wherein the base is present in a concentration so that the aqueous solution has a pH of from about 5 to about 12.

8. The aqueous solution of claim 3, wherein the base is present in a concentration so that the aqueous solution has a pH of from 7 to 10.

9. The aqueous solution of claim 4, wherein the pH control agent is at least one base or at least one acid.

10. The aqueous solution of claim 1, wherein the monochloramine is present in the aqueous solution at a concentration of 1 ppm to 75 ppm, and the at least one peracid is present in the aqueous solution at a concentration of from 1 ppm to 100 ppm.

11. A method of controlling the growth of at least one microorganism in or on a product, material, or medium susceptible to attack by a microorganism, the method comprising treating the product, material or medium with the aqueous solution of claim 1.

12. The method of claim 11, wherein the pH of the aqueous solution or the product, material or medium, or both, is from about 5 to about 12.

13. The method of claim 11, wherein the monochloramine is present in the aqueous solution at a concentration of from 1 ppm to 50 ppm, and the at least one peracid is present in the aqueous solution at a concentration of from 5 ppm to 100 ppm.

14. The method of claim 12, wherein the pH is from 7 to 10.

15. The method of claim 11, wherein the aqueous solution further comprises at least one base.

16. The method of claim 15, wherein the base comprises sodium hydroxide.

17. The method of claim 15, wherein the base is present in a concentration so that the aqueous solution has a pH of from about 5 to about 12.

18. The method of claim 15, wherein the base is present in a concentration so that the aqueous solution has a pH of from 7 to 10.

19. The method of claim 11, wherein at least one pH control agent is present in a concentration so that the aqueous solution has a pH of from about 5 to about 12.

20. The method of claim 15, wherein monochloramine and at least one base are combined in an aqueous fluid before adding the aqueous fluid to said product, material, or medium, and where at least one peracid is further added to the aqueous fluid before the adding or separately applied to the said product, material, or medium.

21. The method of claim 11, wherein said monochloramine is formed in-situ in said medium or in the presence of said product or material.

22. The method of claim 11, wherein the microorganism is a bacterium.

23. The method of claim 11, wherein the material or medium is wood pulp or paper, wood chips, lumber, paints, leathers, adhesives, coatings, animal hides, tanning liquor, paper mill liquor, fiberglass, dairy processing, poultry processing, meat packing facilities, meat processing, metalworking fluids, petrochemicals, pharmaceutical formulations, cooling water, recreational water, dyes, clays, mineral slurries, cationic surfactants, formulations with cationic surfactants, influent water, waste water, pasteurizers, retort cookers, cosmetic formulations, toiletry formulations, textiles, geological, drilling lubricants, or agrochemical compositions for crop or seed protection.

24. The method of claim 11, wherein the material or medium is in the form of a solid, a dispersion, an emulsion, or a solution.

25. A method for preventing or slowing down spoilage of a product, material, or medium caused by microorganism selected from bacteria, fungi, algae, or mixtures thereof, wherein the method comprises applying the aqueous solution of claim 1 to the product, material, or medium.

26. The method of claim 25, wherein the pH of the aqueous solution or the product, material, or medium, or both, is from about 5 to about 12.

27. The method of claim 25, wherein the material is seeds or crops.

28. The method of claim 25, wherein said product is a meat, vegetable, or fruit.

29. The method of claim 25, wherein said product is a food product.

30. The method of claim 25, wherein monochloramine and at least one peracid are applied separately to said product, material, or medium.

31. The method of claim 25, wherein the aqueous solution further comprises at least one base and wherein monochloramine and at least one base are combined in an aqueous fluid before adding the aqueous fluid to said product, material, or medium, and wherein at least one peracid is further added to the aqueous fluid before adding or separately applied to the said product, material, or medium.

32. The method of claim 25, wherein said material or medium is a surface, device, and/or machinery utilized in meat, vegetable, or fruit preparation or processing or packing.

* * * * *